United States Patent [19]

Esper et al.

[11] 4,001,758
[45] Jan. 4, 1977

[54] STOICHIOMETRIC AIR/FUEL RATIO EXHAUST GAS SENSOR

[75] Inventors: Michael J. Esper, Redford Township; Wells L. Green; Stanley R. Merchant, both of Garden City; Charles M. Wells, Livonia, all of Mich.

[73] Assignee: Ford Motor Company, Dearborn, Mich.

[22] Filed: Sept. 2, 1975

[21] Appl. No.: 609,767

[52] U.S. Cl. .............................. 338/34; 23/254 E; 73/27 R; 338/229
[51] Int. Cl.² .......................................... H01L 7/00
[58] Field of Search ............... 338/34, 229; 73/23, 73/27 R; 23/254 E, 255 E, 232 E

[56] References Cited
UNITED STATES PATENTS

| | | | |
|---|---|---|---|
| 3,911,386 | 10/1975 | Beaudoin | 338/34 |
| 3,933,028 | 1/1976 | Laud et al. | 338/34 X |
| 3,959,765 | 5/1976 | Stewart | 338/34 |

*Primary Examiner*—C. L. Albritton
*Attorney, Agent, or Firm*—Robert A. Benziger; Keith L. Zerschling

[57] ABSTRACT

A stoichiometric air/fuel ratio exhaust gas sensor construction particularly useful with variable resistance partial pressure of oxygen responsive sensor material is disclosed. A generally cylindrical mounting body, formed of corrosion resistant material, is arranged for receipt within the exhaust system of an internal combustion engine and is provided with a two-part ceramic insert member for support of a wafer of variable resistance sensor material. The ceramic insert member is comprised of a first portion having a slotted tip for receipt and support of the wafer of partial pressure of oxygen responsive ceramic sensor material. The ceramic insert member is arranged to position the wafer within a perforated shield member at a remote free end of the cylindrical housing body. The wafer includes a pair of extending high temperature resistant electrical conductors which are received within bores provided therefor in the ceramic insert member. The extending leads are electrically connected, proximate to the interface of the two-part ceramic insert member, to a pair of relatively flexible, electrically low resistance, high temperature resistant extending lead wires which are received within the second portion of the ceramic insert member.

7 Claims, 6 Drawing Figures

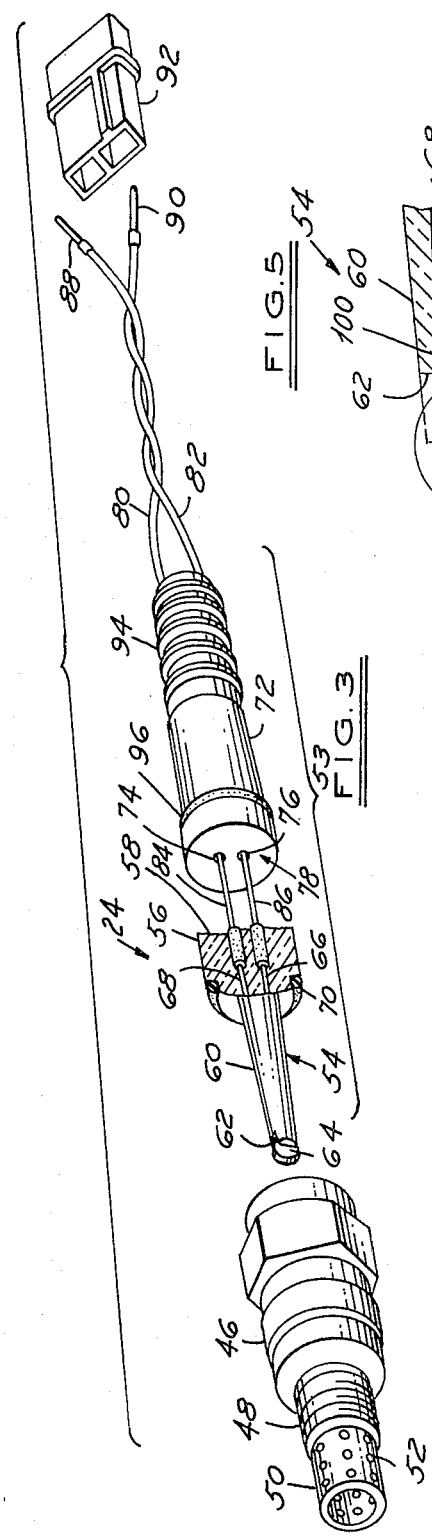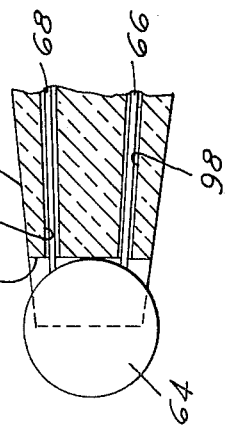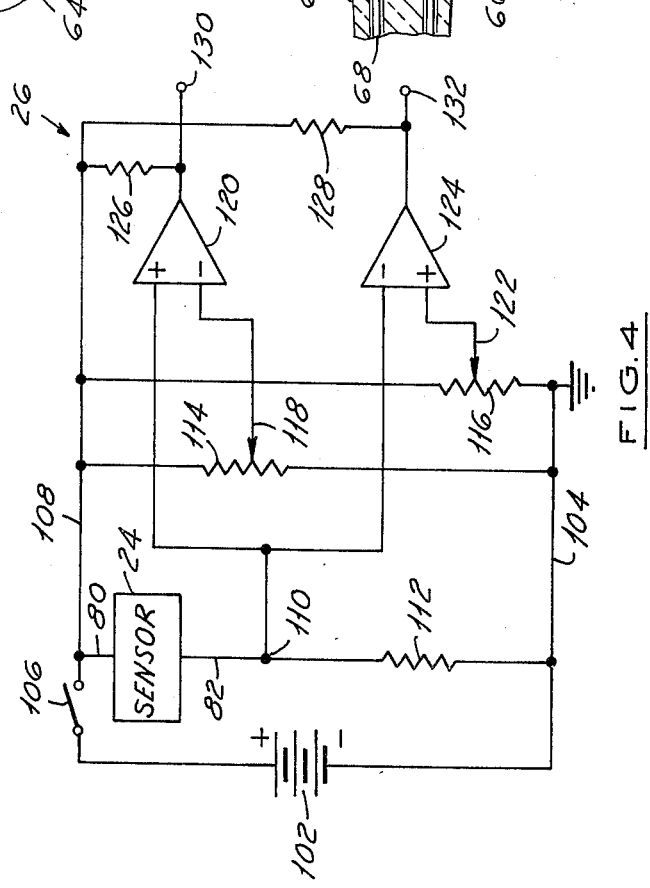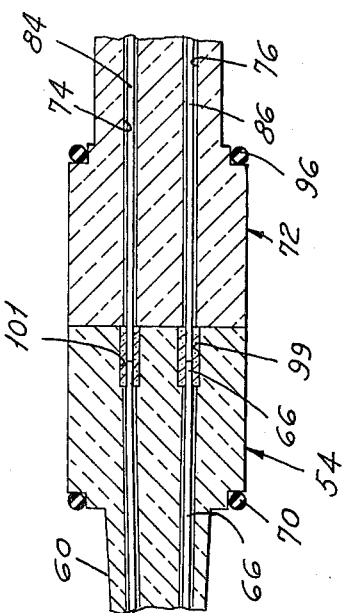

STOICHIOMETRIC AIR/FUEL RATIO EXHAUST GAS SENSOR

CROSS REFERENCE TO RELATED APPLICATIONS

The present invention is related to the subject matter described in copending, commonly assigned patent application Ser. No. 483,723 for Exhaust Gas Sensor and Method of Manufacture filed June 27, 1974 in the names of Gordon L. Beaudoin et al. and Ser. No. 541,365 for Exhaust Gas Air Fuel Ratio Sensor filed Jan. 15, 1975 in the names of Gordon L. Beaudoin et al. as well as the applications referred to therein.

BACKGROUND OF THE INVENTION

1. Field of the Invention

The present invention is directed to the field of exhaust gas chemistry responsive sensors. More particularly, the present invention is directed to that portion of the above-noted field which is concerned with the construction of an exhaust chemistry responsive sensor for insertion in the exhaust system of an automotive internal combustion engine to provide a signal indicative of the air to fuel ratio of the combustion mixture providing the exhaust gases. More particularly still, the present invention is directed to that portion of the above-noted field which is concerned with the provision of an exhaust gas sensor which may be used to indicate a condition of stoichiometry in the combustion mixture which is generating the exhaust gases as a by-product of combustion and which sensor may be used as an input device for an air/fuel ratio controller such that the combustion mixture may be maintained at stoichiometry. More particularly still, the present invention is directed to that portion of the above-noted field which is concerned with providing an exhaust gas chemistry responsive sensor which will be substantially lower in cost and of substantially less complexity than prior exhaust gas sensors.

2. Description of the Prior Art

There are, generally speaking, two classes of exhaust gas sensors. Each makes use of a material which respond principally to the partial pressure of oxygen in the exhaust gases. The first of these, which is exemplified by the use of zirconia as the operative material, responds to a differential partial pressure of oxygen between a reference source of gas such as the atmosphere and a sensed gas to generate a galvanic voltage or electromotive force between the surfaces of the material which are exposed to the two gases, which may be used as a signal. These devices require that the surfaces exposed to the gases be provided with porous electrodes and that one surface be exposed to a relatively constant reference source while the second surface is exposed to the exhaust gases. This requirement presents constructional problems since it is normally the practice to use ambient air as the reference gas and this introduces substantial temperature gradients across the ceramic material. In order to provide rapid response times and for various other desirable operating characteristics, the zirconia material is preferably kept thin. The above-noted requirement and the preferred thinness also present sealing problems as well as other problems of an electrical nature. As a result, this class of devices tends to be fragile, expensive and relatively unreliable after being in use for a term of time less than that required to give an average of about 50,000 driving miles of service.

A second group of exhaust gas chemistry responsive sensors, which may be typified by the use of for example titania ceramic material as the operative material, exhibits an electrical resistance which varies, at elevated temperatures, as a function of the partial pressure of oxygen in the gaseous environment of the ceramic and as a function of temperature. The above-noted copending commonly assigned patent applications describe various titania ceramic exhaust gas sensor configurations which typically utilize an electrical heat source to provide the sensor with an initial heating and to thereafter maintain the sensor at a specific selected elevated temperature so that resistance variations will not be caused by fluctuations in the exhaust temperature.

Electrical heating means are typically provided in the form of an electrical resistance coil formed of platinum conductive wire. Such a heat source contributes substantially to the cost of a sensor, both from the standpoint of the cost of the platinum material and from the standpoint of the manufacturing complexity presented by the necessity of mounting the heater and communicating the heater, through the support ceramic material, to a separate electrical source for energization. Precise temperature control is required to eliminate temperature variations from influencing the sensor signal and to provide a very accurate temperature control particularly for operation of the associated internal combustion engine at nonstoichiometric combustion mixture ratios.

Investigation of the electrical resistance versus air/fuel ratio response curve of titania exhaust gas sensors has indicated that the resistance value of the titania varies substantially for the exhaust by-products of combustion mixtures which experience a lean to rich or rich to lean excursion or transition. In many instances, this variation may be several orders of magnitude, even in the face of adverse temperature variations. It is therefore an object of the present invention to provide a titania-based exhaust gas partial pressure of oxygen sensor to operate in the exhaust system of an engine operated with a combustion mixture having a stoichiometric air/fuel ratio which is low in cost and relatively simple to assemble.

One continuing objective which the automotive industry in general has in fabricating any power train related component is maximum durability. The federal law has further stimulated the automotive industry to attempt to obtain, in the case of pollution control related engine components such as an exhaust gas sensor for use in a feedback air/fuel ratio control system, a durability factor which would be equivalent to operation of the average vehicle over approximately 50,000 miles. Under such a requirement, an exhaust gas sensor would be required to undergo a large number of thermal cycles and considerable vibration as well as being required to withstand the extremes of seasonal weather contaminates to which a vehicle may be subjected. Such a device, in order to be cost effective, would have to achieve the desired level of operation and reliability while maintaining as low a cost as possible. Since the sensor and its associated mechanical hardware would be subjected to the high temperature environment of the exhaust system and could be expected to be subjected to exposure to road salt and the like it would be necessary that the electrical portion of the sensor be capable of withstanding thermal cycling in the presence of a salt environment. Conventional means of thermal and environmental insulation would not normally be expected to hold up to this type of environment and the number of electrical leads associated with the exhaust gas sensor would multiply the statistical chances of failure. It is therefore a further and specific object of the present invention to provide an exhaust gas chemistry responsive sensor requiring only a pair of electrical leads which may be arranged in such a fashion as to assure maximum protection against salt, road spray and splash. While these objectives can be achieved with the sensor construction according to the prior art by merely adding substantial insulation, this approach would greatly increase the cost and complexity of the devices. It is therefore a further and specific objective of the present invention to provide a low cost, low complexity exhaust gas sensor of the variable resistance type to operate as a stoichiometry indicator in an exhaust gas feedback responsive air/fuel ratio controller. More particularly still, it is an object of the present invention to provide an exhaust gas sensor of rugged construction which is low in cost and which is of sufficiently simple construction that it may be manufactured on largely automated machinery.

Since the partial pressure of oxygen responsive sensor must be connected to further electrical apparatus in order to provide input information, for example for the air/fuel ratio controller, the sensor must be provided with an electrical terminal which is plug compatible with this further apparatus. The leads normally embedded within the variable resistance sensor material are typically platinum. It is relatively very expensive to extend the platinum material all the way from the sensor wafer to the terminal. It therefore is necessary to provide an interconnection between the sensor wafer leads and the terminal leads as close to the wafer as possible in order to minimize the quantity of platinum conductor required for each sensor device. This interconnection must provide for ideal electrical contact between the sensor leads and the terminal leads, must be readily accomplished during manufacture of the sensor, and must be capable of withstanding the high temperature environment of the sensor device and the thermal cycling of the sensor device. The normal approach to designing an exhaust gas sensor for reduced cost and potential automated assembly would be to minimize the number of components and to place all connections between electrical conductors at the rear of the device to reduce temperature effects. However, exhaust gas sensors fabricated according to this philosophy have exhibited electrical failures resulting from shorts occurring at the electrical interconnections. These electrical shorts occurred in part as a consequence of the accumulation of material over a long period of time in the vicinity of the electrical interconnections. It is therefore a specific object of the present invention to provide a low cost, durable exhaust gas sensor construction which avoids the use of interconnections between electrical conductors exterior of the device. It is also an object of the present invention to provide an exhaust gas chemistry responsive sensor which intercommunicates a wafer of variable resistance exhaust gas chemistry responsive material with an electrical terminal in such a manner that cost and manufacturing complexity of the end device may be minimized while providing for an electrical interconnection between a precious metal conductor material and less expensive conductor material which may be accomplished within the body of the wafer support ceramic material without adversely altering the capability of the device to withstand extremes in temperature and thermal cycling.

SUMMARY OF THE PRESENT INVENTION

The present invention provides an exhaust gas chemistry responsive sensor having a metallic outer body adapted for threaded connection to a suitable land or boss on the exhaust system of vehicle internal combustion engines for inserting and supporting a wafer of variable resistance exhaust gas chemistry responsive material within the exhaust system. The housing body is provided with an apertured end portion which operates to generally shield the sensor chip from the exhaust stream. The sensor device further includes a first and second ceramic body with the first ceramic body having a generally conical portion which is slotted at a remote end and has a pair of internally extending passages which receive the electrical leads, typically formed of a precious metal such as platinum, from the sensor wafer. The sensor wafer is received in supported fashion within the slotted end portion of the first ceramic body. The first ceramic body of the ceramic insulator means is sealingly received within the metallic outer body. A pair of conductive leads is received within a second ceramic body of the ceramic insulator means and extends through a pair of passages provided therefor. One end of each of said pair of wires is provided with an electrical connector or terminal means and the other end of each of said pair of wires is electrically connected to a corresponding one of said pair of wafer leads with said interconnection being proximate to the interface of said first and second ceramic bodies. The second ceramic body is also received within the outer metallic body in sealed relation thereto.

In manufacture, the sensor chip is positioned within the slotted end portion of the first insulator member while the wafer electrical leads are received within the passages provided therefor within the first ceramic body and the first ceramic body is deposited within the outer body for example in suspended relation. The electrical terminal leads are fed through the passages provided therefor in the second ceramic body and are inserted into the rear face portions of the passages within the first ceramic body. Relatively high temperature melting, electrically conductive material is deposited thereabout and the second insulator body is supported on the rear face of the first insulator body. The insulator bodies are thereafter subjected to localized heating sufficient to flow the material and to establish a mechanically strong and electrically highly conductive interconnection between the sensor wafer leads and the electrical terminal leads. The composite structure is thereafter provided with suitable seal means and the sensor metallic outer body is crimped to maintain the ceramic bodies in tightly sealed relation with respect to the outer body.

BRIEF DESCRIPTION OF THE DRAWINGS

FIG. 3 illustrates the exhaust gas chemistry responsive sensor apparatus according to the present invention in an exploded view.

FIG. 4 illustrates one representative electrical circuit which may respond to the sensor apparatus of FIG. 3 to provide an output signal for controlling the air/fuel ratio controller illustrated in FIG. 1.

FIGS. 5 and 6 are enlarged, fragmentary, partially sectioned views of portions of the sensor apparatus according to FIG. 3 illustrating various features of the instant invention.

DETAILED DESCRIPTION OF THE PREFERRED EMBODIMENT

Figure 1:
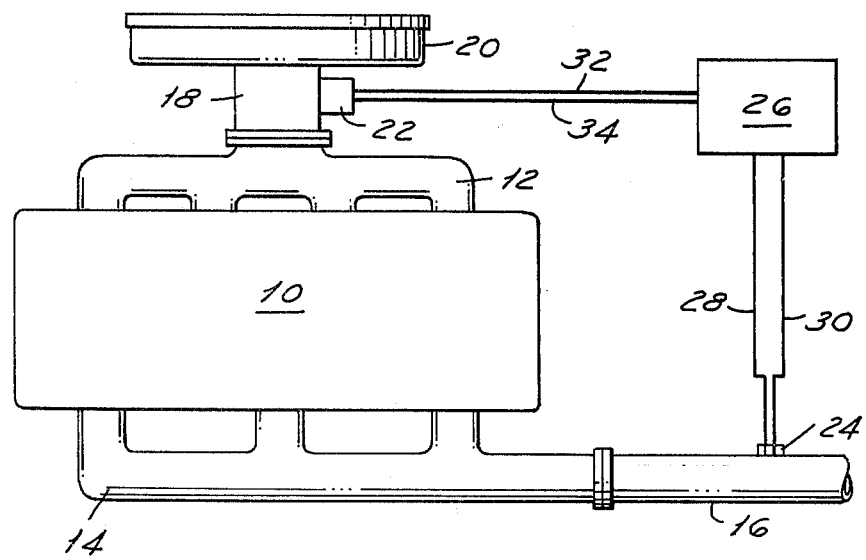
FIG. 1 is a schematic diagram illustrating an internal combustion engine having an exhaust responsive feedback air/fuel ratio control mechanism with which the present invention is of utility.

Referring now to FIG. 1, an internal combustion engine 10 is illustrated. Internal combustion engine 10 is provided with an intake manifold 12 and an exhaust manifold 14. Exhaust manifold 14 communicates with an exhaust gas conduit 16. A fuel metering and delivery device 18, which may be for example a fuel injection system or a carburetor, is illustrated schematically communicating with the intake end of intake manifold 12. Fuel metering and delivery device 18 is provided with an air cleaner 20 such that air ingested by engine 10 through intake manifold 12 may be drawn from the atmosphere through air cleaner 20 and through at least a portion of the fuel metering and delivery device 18. The construction, purpose and operation of the hereinabove set forth structure is well known and further description is considered to be unnecessary.

Fuel metering and delivery device 18 is also provided with an air/fuel ratio modulator means 22. Air/fuel ratio modulator means 22 may be for example, in the case of an electronic fuel injection system, a variable resistor arranged to control the quantity of fuel delivered to engine 10 in relation to a given quantity of air or, in the case of a carburetor, may be a variably positionable metering valve arranged to control the quantity of fuel metered to engine 10 in respect of a given quantity of air. The air/fuel ratio modulator means 22 may alternatively be arranged to control a variably positionable air valve so that the quantity of air ingested by engine 10 in respect of a given quantity of fuel delivered by fuel metering and delivery device 18 may be modulated.

Exhaust gas conduit 16 is provided with an exhaust gas sensor 24 which is mounted on a suitable land or boss on conduit 16 so as to expose an exhaust gas chemistry responsive sensing element to the exhaust gases flowing through conduit 16. As used throughout this description, "exhaust gas sensor" is intended to mean a device or apparatus connected to an exhaust system for responding to the chemical constituents of the exhaust gases and which includes a solid ceramic wafer or chip with an electrical resistance which varies in response to variations in a chemical constituent of the exhaust gases which, in turn, varies directly with and as a result of variations in the air/fuel ratio of the combustion mixture which produces the exhaust gases as a by-product of combustion. Exhaust gas sensor 24 communicates with electronic control means 26 through a pair of sensing leads 28, 30. Electronic control means 26 also communicates with the air/fuel ratio modulator means 22 through conductive controller leads 32, 34. As described hereinbelow with reference to FIG. 4, the electronic control means 26 may be arranged to respond to changes in the exhaust gas chemistry which are sensed by exhaust gas sensor 24 to provide control signals for receipt by the air/fuel ratio modulator means 22 which control signals may be arranged to modulate either the air or the fuel content and hence the air/fuel ratio of the combustion mixture being provided to internal combustion engine 10 to thereby maintain a desired exhaust gas chemistry. It will be appreciated that the exhaust gas sensor 24 could also be mounted on a suitable land or boss on exhaust manifold 14.

Figure 2:
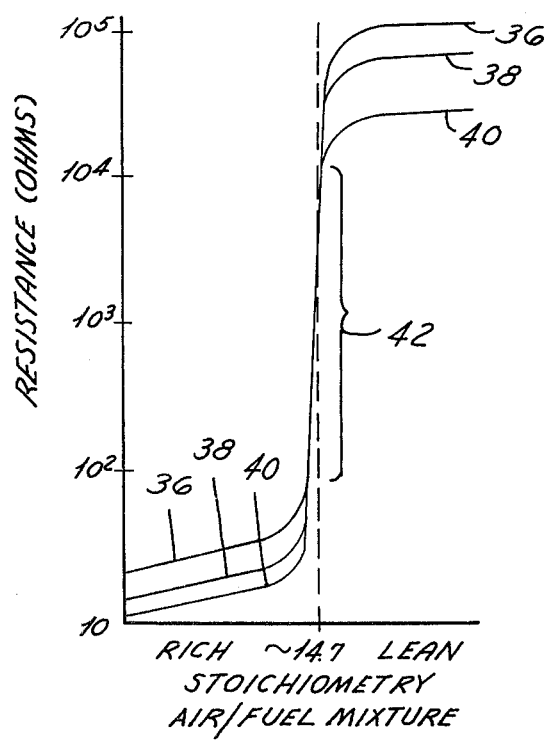
FIG. 2 illustrates representative resistance versus air/fuel ratio mixture curves which typify the electrical behavior of the variable resistance exhaust gas chemistry responsive materials.

Referring now to FIG. 2, three resistance versus air/fuel ratio curves are graphed to illustrate the resistance response of a representative variable resistance exhaust gas chemistry responsive material at three different operating temperatures. The curves are identified as 36, 38 and 40 with curve 36 being the lowest temperature resistance curve and curve 40 being the highest temperature resistance curve. In the region denoted by numeral 42 it can be seen that the curves generally overlap and are nearly vertical. In each instance this corresponds approximately with the vertical line 44 which is indicated as an air/fuel ratio of 14.7 and is here indicative of stoichiometry. This region of overlap represents a significant change of resistance as can be seen but corresponds to a change in air/fuel ratio of only about ±0.1 air/fuel ratios. The specific air/fuel ratio for stoichiometry will be a function of the chemical composition of the particular fuel mixture being used and in normally available gasolines may range from approximately 14.6 to approximately 14.8. The curve 36 corresponds with the resistance variation observed in an exhaust gas chemistry sensor subjected to a transition of mixture ratios from the rich (fuel in excess of that required for complete conbustion in a given quantity of oxygen) to the lean (oxygen in excess of that required for complete combustion of a given quantity of fuel) at relatively low elevated temperature, for example about 500° C. The resistance curve 40 corresponds to a resistance change which occurred under similar operating conditions at higher elevated temperature conditions, for example for about 900° C. Curve 38 represents a similar transition for an intermediate temperature. The range of temperatures expected to occur in a typical exhaust system ranges from the lowest elevated temperature at which the exhaust gas sensor would function, about 400° C, to a maximum temperature of about 1000° C. It can be seen that for both the high temperature and the low temperature transitions, a resistance change substantially in excess of two orders of magnitude occurs with an air/fuel ratio transition from slightly rich to slightly lean. In will therefore be appreciated that the exhaust gas sensor 24 may readily be arranged to maintain the air/fuel ratio very close to the stoichiometric ratio by attempting to modulate that ratio and maintain its own internal resistance at a value which approximates a selected point, for example the middle, of the range identified by numeral 42.

Referring now to FIG. 3, an exhaust gas sensor 24 fabricated according to the present invention is illustrated. Exhaust gas sensor 24 comprises a metallic outer, or mounting, body 46 having a threaded end portion 48 and a projecting, generally cylindrical, shield portion 50 which is perforated as at 52. A ceramic insert means 53 comprising a first ceramic member or body 54 is provided with a relatively large diameter cylindrical portion 56 having a rear face 58. A generally conical portion 60 projects from cylindrical portion 56 and is provided with a slotted end 62. The height of the conical portion may be a function of the desired depth of insertion within any particular exhaust gas system. A wafer or disc of variable resistance exhaust gas chemistry responsive ceramic material 64, which is preferably fabricated of titania according to the procedures described in issued U.S. Pat. No. 3,886,785, is received within slotted end 62. In fabricating the variable resistance ceramic disc 64, a pair of resistance sensing leads are embedded therein in spaced-apart, mutually noncontacting, relation and are arranged to extend away from the ceramic portion 64. First ceramic body 54 is provided with at least a pair of passages which extend from rear face 58 through conical portion 60 to the slotted end 62 and are arranged for receipt of the leads extending from wafer 64, here illustrated as leads 66, 68. As shown in this view, a seal member 70 is received within a suitably provided gasket seat at a forwardly positioned extending shoulder of cylindrical portion 56. As a matter of convenience in describing positional relationships, "forward" refers to a direction toward the wafer 64 while "rearward" refers to a direction away from wafer 64. Second ceramic body or portion 72 of ceramic insert means 53 is provided with a pair of through passages 74, 76 which communicate the forward face 78 with the rearward face 79 of the second ceramic body 72. A pair of individually insulated electrical conductors 80, 82 are received within through passages 74, 76 and are arranged so that the conductor members thereof, 84, 86 may extend through passages 74, 76 and be affixed in direct electrical communication with sensor leads 66, 68. The pair of insulated conductors 80, 82 are provided at their free ends with a pair of electrical terminal members 88, 90 which are adapted for receipt within an electrical conductor body 92. In this way, the sensing wafer 64 may be placed in electrical communication with the electrical controller means 26 by way of a convenient plug-in electrical connector. Second ceramic body 72 is also provided with a plurality of heat dissipating fin members longitudinally placed along the rear portion thereof and arranged to extend generally radially away from the center line of second ceramic body 72, as at 94, in order to reduce the amount of heat to which the insulated conductors 80, 82 and the electrical connector body 92 would be exposed in normal operation.

Referring now to FIG. 4, the electrical controller means 26 is illustrated in a specific circuit embodiment. This circuit embodiment is merely illustrative and a large number of other circuit arrangements would be applicable for use with the exhaust gas sensor construction according to the invention.

A source of electrical energy, such as battery 102, is provided to energize the circuit. Battery 102 is arranged to have its negative terminal connected to the ground or common conductor 104, as is normally the case in domestic manufacture automobiles. The positive terminal of battery 102 is connected through switch 106 to a high voltage conductor 108. Switch 106 may be, for example, a portion of the ignition switch of the vehicle in which internal combustion engine 10 is installed. Exhaust gas sensor 24 is electrically communicated to the high voltage conductor 108 by insulated conductor 80 while insulated conductor 82 communicates exhaust gas sensor 24 with a junction 110. Resistor 112 communicates junction 110 with the ground 104. A pair of variable potentiometers 114, 116 are arranged in parallel between the high voltage conductor 108 and the ground 104. The voltage tap 118 of variable potentiometer 114 is connected to one input terminal of voltage comparator 120 while the voltage tap 122 of variable potentiometer 116 is connected to one input terminal of voltage comparator 124. The voltage taps 118, 122 are connected to input terminals of opposite polarity such that, for example, voltage tap 118 is connected to the negative polarity input terminal of its associated voltage comparator 120 while voltage tap 122 is connected to the positive polarity input terminal of its associated voltage comparator 124. Junction 110 is communicated to the remaining two input terminals of the voltage comparators 120, 124.

As illustrated, the comparators 120, 124 are of the type having an internal output transistor which is either conductive or nonconductive depending on the character of the inputs applied to the comparator. If the potential applied to the positive input terminal of such a comparator is higher than the potential applied to its negative input, then the internal output transistor is rendered nonconductive and the associated pull-up resistor 126, 128 will apply substantially the potential of high voltage conductor 108 to the output terminal 130, 132 thereof. If the negative input of such a comparator is higher in potential than the potential applied to its positive input terminal, then the internal output transistor is rendered conductive and the voltage on the output lead thereof will be at substantially the ground potential.

With reference now to FIGS. 2 and 4, the operation of the circuit of FIG. 4 in association with the sensor according to the present invention will be explained. A representative resistance value is selected from the curves of the FIG. 2 graph. For example, a resistance value of twelve hundred ohms (1200 Ω) may represent the selected operating point within the range 42. Resistor 112 is selected to have a value such that the voltage appearing at junction 110 will be a predeterminable known quantity when the resistance of the sensor wafer 64 is at the selected point in range 42. By way of example, resistor 112 may be selected to be a twelve hundred ohm resistor so that, under design conditions, the voltage at the junction 110 will be one-half of the supply voltage of battery 102. This sensor voltage at junction 110 will be applied to the positive input terminal of comparator 120 and to the negative input terminal of comparator 124.

Variable potentiometer 114 may have its center tap 118 adjusted to apply a voltage to the negative input terminal of comparator 120 which is slightly more positive than the voltage calculated to appear at junction 110 when the combustion mixture supplied to the associated engine is at the value corresponding to the selected point in range 42 and therefore may represent the maximum permissible drift of the air/fuel ratio of the combustion mixture into the rich region. Variable potentiometer 116 may have its voltage tap 122 adjusted to apply a voltage at the positive input terminal of voltage comparator 124 to be slightly less than the voltage appearing at junction 110 under conditions corresponding to operation of the engine at an air/fuel ratio corresponding to the selected resistance value of sensor 24 within the range 42. This may therefore control the maximum drift of the air/fuel ratio into the lean region. Therefore, so long as the combustion mixture is being provided to the engine at, or very close to, the air/fuel ratio corresponding to the selected resistance value of the sensor wafer 64 the voltage comparators will be biased to an off and nonoperative condition. Lack of a signal appearing at output terminals 130, 132 may therefore operate to maintain the air/fuel ratio modulator means 22 in a static condition and the air/fuel ratio of the combustion mixture being provided to the engine will not vary. If for some reason the fuel content of the combustion mixture increases (a rich air/fuel mixture), the resistance of the sensor 24 will decrease and the voltage appearing at junction 110 will increase. When this increase is sufficiently large to indicate that the air/fuel ratio has drifted into the rich region beyond that point for which operational drift is permitted, as established by the set point of variable potentiometer 114, voltage comparator 120 will generate a high voltage which may represent an output signal. Such a signal may initiate change of, or may be used to directly modulate, the setting of the air/fuel ratio modulator means 22 to begin to decrease the fuel content of the combustion mixture. As fuel content decreases, the resistance of the sensor wafer 64 will increase to the point that the voltage appearing at junction 110 will decrease to eventually remove any voltage signal at terminal 130.

If for some reason the fuel content of the combustion mixture decreases, the sensor resistance will begin to increase and comparator 124 will generate an output signal at terminal 134 to initiate an increase in the fuel content of the combustion mixture. It will be appreciated that selection of components will depend in large part upon the nature of the control electronics and upon the exact form of air/fuel ratio modulator means 22. If the air/fuel ratio modulator means requires a certain form of signal (for example a high current or ground voltage signal), the comparator means 120, 124 may be selected accordingly with other component values being dictated thereby.

Referring now to FIG. 5, an enlarged, fragmentary, partly sectioned view of the sensor wafer 64 and the slotted end of conical portion 60 of first ceramic body 54 is shown. As can be seen from this view, sensor wafer 64 has a pair of sensor leads 66, 68 which extend away therefrom and which are received within passages 98, 100 provided therefor in first ceramic body 54. Passages 98, 100 communicate the slotted end 62 with the rear face 58 of first ceramic body 54. Sensor wafer 64 is received within slotted end 62 and is retained within slotted end 62 by the action of the sensor leads 66, 68. Slotted end 62 is preferably wide enough to receive sensor wafer 64 in a loose fit condition so as to avoid the application of clamping pressure to sensor wafer 64 which, over the long term, may have deleterious effects. Alternatively, sensor wafer 64 could be cemented into position within slot 62 through the use of a nonreactive titania or zirconia-based cement. In either circumstance, it is important that only a small portion of sensor wafer 64 be masked or shielded from contact with the flowing exhaust gases and to that end, slot 62 has only a shallow depth with respect to the dimensions of wafer 64. In the case of a circular configuration sensor wafer 64, only a minor arcuate portion of sensor wafer 64 is received within slot 62. As here illustrated, passages 98, 100 are arranged to be parallel to each other and to the approximate center line of first ceramic body 54. It would also be feasible to have passages 98, 100 arranged to be slightly divergent from each other in the rearward direction with size and spacing arranged to provide for proper spatial relationship between the passage orifices on the rear face 58 and the passage orifices on the forward face 78 of the first and second ceramic bodies, respectively.

Referring now to FIG. 6, an enlarged, fragmentary, partly sectioned view of the ceramic insert means 53, illustrating the electrical union between sensor leads 66, 68 and conductive leads 84, 86 is illustrated. As shown in this view, the passages 98, 100 provided within the first ceramic body 54 are provided with enlarged portions 99, 101 within cylindrical portion 56 and proximate to the rear face 58 of the first ceramic body. Sensor leads 66, 68 are of a length sufficient to permit them to extend from the slotted end 62 into the enlarged passage portions 98, 100. Conductors 84, 86 extending through passages 74, 76 of the second ceramic body 72 are arranged, when rear face 58 is in abutment with forward face 78 to extend into the enlarged passage portions 98, 101.

In assembly of the exhaust gas sensor 24 according to the present invention, and with particular reference to FIGS. 3, 5 and 6, sensor wafer 64 having a pair of extending sensor leads 66, 68 is received within slotted end 62 so that sensor leads 66, 68 extend through passages 98, 100 and their remote free ends are positioned within enlarged passage portion 99, 101. Passage portions 99, 101 are thereafter filled with a powder of, for example, a copper or metallic flake brazing compound. Concomitantly, the insulated conductors 80, 82 are inserted into the rear face 79 of second ceramic body 72 and the conductive leads 84, 86 are arranged to extend completely through passages 74, 76. The conductive leads 84, 86 are thereafter forced into the powder-filled passage portions 99, 101 and the forward face 78 of second ceramic body 72 is brought into abutment with the rear face 58 of first ceramic body 54. Thereafter, localized heating is applied to cylindrical portion 56 of first ceramic body 54 to provide sufficient heat energy to cause the powdered material within passage portions 99, 101 to flow in order to provide an electrically conductive, mechanically strong, union between sensor leads 66, 68 and the conductors 86, 84, respectively. The ceramic insert means 53 is thereafter inserted within the metallic outer body 46 to place forward seal in abutment with a sealing surface provided therefor on the interior of metallic outer body 46. The rear portion of metallic outer body 46 is then crimped to apply sealing pressure to rear seal 96. Alternatively, rear seal 96 may be replaced by a ceramic seat in those instances where adequate sealing will be provided by the forward seal 70 cooperating with the metallic outer body 46.

Terminal members 88, 90 and connector body 92 may be added to the insulated conductors 80, 82 at any point during the manufacturing process and may be applied to the insulated conductors 80, 82 prior to the insertion of the conductors 80, 82 within second ceramic body 72.

The material selected for the heat flowable powder should be selected to be electrically highly conductive and to be capable of forming a mechanically strong bond with the material of the sensor leads 66, 68 which are typically platinum and the material of the conductors 84, 86 which would be a high temperature alloy such as chromel. The heat flowable material should also seal passages 74, 76 and 98, 100 to prevent exhaust gases from flowing therethrough. Furthermore, the material selected for the heat flowable powder should be capable of withstanding, without flowing, the normal operating temperature of the exhaust system in which the sensor 24 is to be utilized and should have a coefficient of thermal expansion which is approximately equal to the coefficient of thermal expansion of the ceramic material which forms the first and second ceramic bodies and with the material of the sensor leads 66, 68 and conductors 84, 86. The ceramic material forming the first and second ceramic bodies is typically a high alumina content ceramic material.

It can be seen that the present invention readily accomplishes its stated objectives. By providing a conical portion having a slotted end into which the sensor wafer is to be loosely inserted, the sensor wafer may be supported in such a manner that a maximum surface area is free for exposure to the exhaust gases in the exhaust system. This allows the total sensor volume to be reduced to a minimum constanant with good thermal response, electrical insulation between the lead wires embedded within the sensor material and rapid response to changing air/fuel ratios. By arranging for interconnection between the precious metal sensor lead wires and the extending conductors which are arranged for connection to remote electrical circuitry at a location proximate to the interface between the first and second ceramic bodies the use of precious metal is reduced to an absolute minimum thereby reducing the cost of the end device. By providing this interconnection within a two-piece ceramic insert means at a location which will eventually be interior to the metallic outer body, this interconnection can be sealed from the atmosphere and from the environment to provide for protection of the interconnection from any long term corrosion effects which might be produced by the combination of heat, cold, and accumulated dirt deposits normally encountered in an automobile. By utilizing the two-piece ceramic insert means with the electrical interconnection between the sensor lead wires and the extending conductors proximate to the interface between the two members of the ceramic insert means, the exhaust gas sensor according to the present invention maintains the desired fabricability on automated machinery with a minimum of hand operations in the assembly of the exhaust gas sensor. By arranging the insulated conductive covering of insulated conductors 80, 82 to actually extend into the interior of the rear of second ceramic body 72 the likelihood that accumulation of foreign matter on the rear face 79 will constitute a short circuit between conductors 84, 86 is greatly reduced since that will also require that the insulated covering be broken on each of the conductors 84, 86. Such a covering may be typically a polytetrafluoroethylene insulator which material is known for its ruggedness and nonreactibility.

We claim:

1. A partial pressure of oxygen sensor for insertion into the exhaust system of an internal combustion engine comprising in combination:

a mounting body formed of durable metallic material threaded on one end for securement to the exhaust system and having a bore extending therethrough;

a first ceramic body received within said mounting body bore and extending therethrough having a slotted tip, an oppositely positioned rear face, and a pair of passages extending away from said slotted tip to said rear face;

a wafer of partial pressure of oxygen responsive ceramic material received within said slotted tip and having a first pair of conductors attached thereto in spaced-apart relationship;

said conductors extending through said first ceramic body passages away from said slotted tip to a point proximate to said rear face;

a second ceramic body having a pair of passages extending therethrough arranged in abutting relationship with said first ceramic body rear face, said first ceramic body passages and said second ceramic body passages being in alignment;

a second pair of conductors received with said second ceramic body passages;

heat flowable material deposited in said passages proximate said rear face for connecting one end of said second pair of conductors to said first pair of conductors; and electrical terminal means connected to the other end of said second pair of conductors.

2. The sensor of claim 1 wherein said mounting body includes an extending sleeve portion extending from the threaded portion and said wafer does not project from said first ceramic body beyond said sleeve portion.

3. The sensor of claim 2 wherein said sleeve has a sidewall and includes a plurality of ports extending through said sidewall.

4. The sensor of claim 1 wherein said heat flowable material includes metallic particles for forming a mechanically strong electrically conductive union between said wafer conductors and said second pair of conductors.

5. The sensor of claim 4 wherein said heat flowable material is deposited in said passages in powder form and is subsequently flowed by the application of heat to attain a temperature in excess of the temperature expected to be attained by the exhaust system.

6. The sensor of claim 1 wherein said first ceramic body includes a shoulder portion defining a gasket seat and including further seal means received within said gasket seat operative to prevent the combustion by-products from flowing through said mounting body bore.

7. The sensor of claim 1 wherein said wafer is a disc-shaped body and is received within said slot such that a minor arc length of the periphery of said disc-shaped body is within said slot.

* * * * *